United States Patent
Karkar et al.

[11] Patent Number: 6,139,554
[45] Date of Patent: Oct. 31, 2000

[54] MULTIPURPOSE TISSUE RESURFACING HANDPIECE

[76] Inventors: Maurice N. Karkar, 26842 Calle Maria, Mission Viejo, Calif. 92691; John I. Muri, 46 Edmonton Pl., Aliso Viejo, Calif. 92656

[21] Appl. No.: 09/329,666

[22] Filed: Jun. 10, 1999

[51] Int. Cl.$^7$ .................................................. A61B 17/50
[52] U.S. Cl. ............................................. 606/131; 606/132
[58] Field of Search .................................... 606/131, 132, 606/159; 604/289, 290, 313, 315

[56] References Cited

U.S. PATENT DOCUMENTS

| | | | |
|---|---|---|---|
| 3,476,112 | 11/1969 | Elstein | 606/132 |
| 3,589,363 | 6/1971 | Banko et al. | |
| 4,316,465 | 2/1982 | Dotson, Jr. | |
| 4,900,316 | 2/1990 | Yamamoto | 604/313 |
| 5,037,432 | 8/1991 | Molinari | |
| 5,112,300 | 5/1992 | Ureche | |
| 5,222,959 | 6/1993 | Anis | |
| 5,224,942 | 7/1993 | Beuchat et al. | |
| 5,346,469 | 9/1994 | Ikeda et al. | |
| 5,433,702 | 7/1995 | Zelman et al. | |
| 5,454,808 | 10/1995 | Koop et al. | |
| 5,458,596 | 10/1995 | Lax et al. | |
| 5,492,528 | 2/1996 | Anis | |
| 5,558,666 | 9/1996 | Dewey et al. | |
| 5,569,242 | 10/1996 | Lax et al. | |
| 5,628,744 | 5/1997 | Coleman et al. | |
| 5,634,933 | 6/1997 | Mccombs et al. | |
| 5,674,235 | 10/1997 | Parisi | |
| 5,722,945 | 3/1998 | Anis et al. | |
| 5,730,718 | 3/1998 | Anis et al. | |
| 5,735,535 | 4/1998 | MCombs et al. | |
| 5,827,292 | 10/1998 | Anis | |
| 5,833,704 | 11/1998 | McCombs et al. | |
| 5,879,376 | 3/1999 | Miller | |
| 5,971,999 | 10/1999 | Naldoni | 606/131 |

FOREIGN PATENT DOCUMENTS

| | | | |
|---|---|---|---|
| 3-267053 | 11/1991 | Japan | 606/131 |

*Primary Examiner*—Paul J. Hirsch
*Assistant Examiner*—Michael B. Priddy
*Attorney, Agent, or Firm*—Price Gess & Ubell

[57] ABSTRACT

A multipurpose handpiece for use with an abrasive material delivery system is disclosed wherein the handpiece includes channels for delivery and removal of an abrasive material applied to a patient's skin. The invention includes a multiport applicator for selectively applying the abrasive material, said application of abrasive material suited for different areas of tissue such as stomach versus eye lids. The present invention comprises a pair of tubings connected to a housing for delivery and vacuum removal of abrasive material, and a flow regulator disposed within the housing. Connected to the housing at an application end is a resurfacing applicator with a plurality of differing sized openings designed for different types of tissue. The present invention includes means for blocking the unused openings while permitting injection of the abrasive material through a selected opening. The blocking of the unused openings may be achieved by a shield or covers for each opening. The present invention is further adapted to stop the flow of the abrasive material while the openings are being changed, and means are provided for rotating the resurfacing applicator, and for aligning the resurfacing applicator opening with the injection port of the flow regulator for even and uninterrupted flow of material.

8 Claims, 4 Drawing Sheets

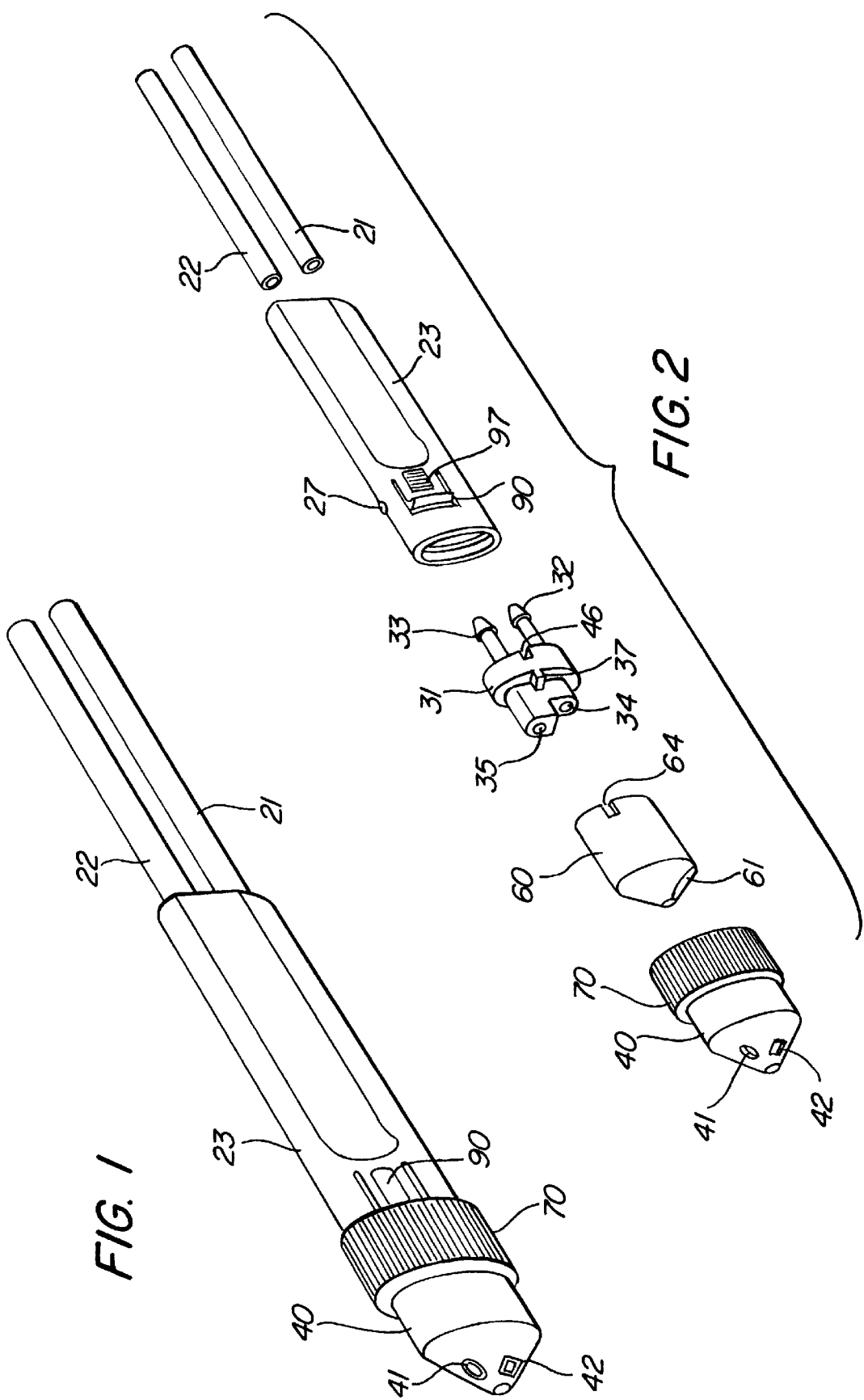

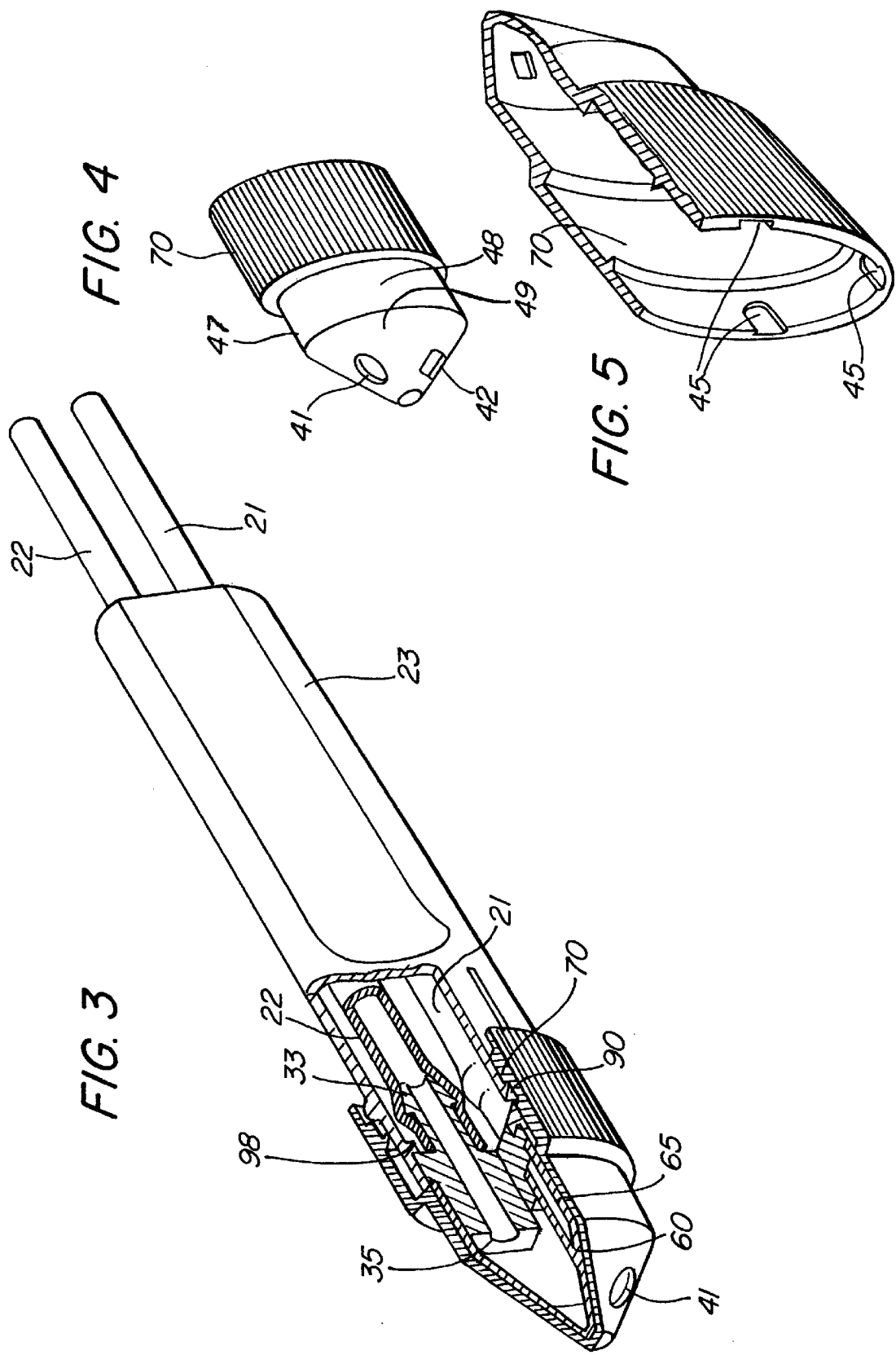

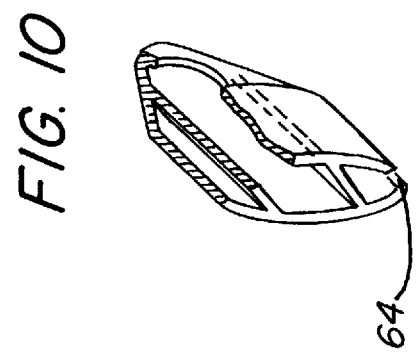
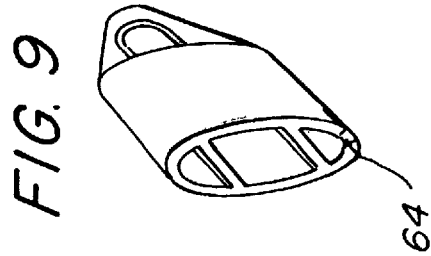
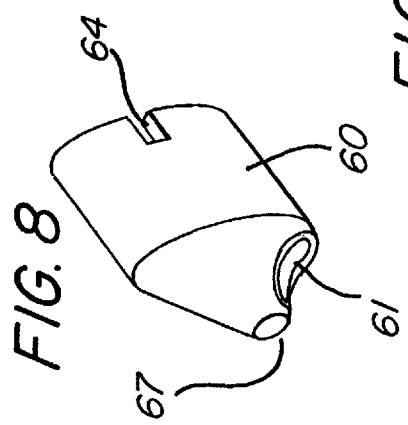
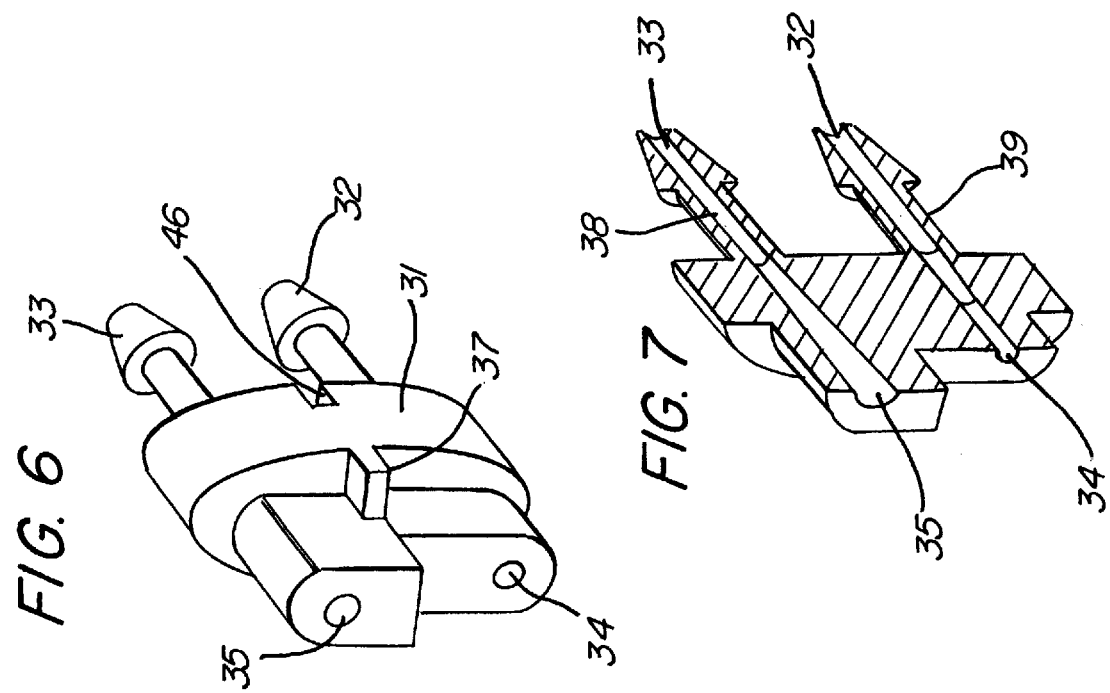

MULTIPURPOSE TISSUE RESURFACING HANDPIECE

BACKGROUND OF THE INVENTION

1. Field of the Invention

The present invention relates generally to a handpiece for tissue resurfacing using an application of an abrasive material, and more particularly to a handpiece with multiple openings of different sizes to accommodate resurfacing of different tissue surfaces.

2. Description of Related Art

Handpieces for electrical, surgical, laser, ultrasonic applications and those used for resurfacing skin tissue are well known. Examples of such applicators are provided in U.S. Pat. No. 5,569,242 issued on Oct. 29, 1996 to Lax, Ronald G. and entitled METHOD AND APPARATUS FOR CONTROLLED CONTRACTION OF SOFT TISSUE; U.S. Pat. No. 5,833,704 issued on Nov. 10, 1998 to McCombs et al. and entitled POWERED HIGH SPEED ROTARY SURGICAL HANDPIECE CHUCK AND TOOLS THEREFORE; U.S. Pat. No. 5,827,292 issued on Oct. 27, 1998 to Anis, Aziz Yehia and entitled REMOVAL OF TISSUE; U.S. Pat. No. 5,433,702 issued on Jul. 18, 1995 to Zelman et al. and entitled PHACO HANDPIECE PROVIDING FINGERTIP CONTROL OF ULTRASONIC ENERGY; U.S. Pat. No. 5,558,666 issued on Sep. 24, 1996 to Dewey et al. and entitled HANDPIECE FOR PRODUCING HIGHLY COLLIMATED LASER BEAM FOR DERMATOLOGICAL PROCEDURES; U.S. Pat. No. 5,037,432 issued on Aug. 6, 1991 to Molinary et al. and entitled ADJUSTABLE APPARATUS FOR REMOVING SURFACE PORTIONS OF HUMAN TISSUE.

Lax's patent discloses the use of a handpiece with an electrode to contract tissue. McCombs et al.'s patent discloses a replaceable high speed surgical handpiece having a centrifugal chuck for pull-out release of such a tool. Anis' patent discloses a surface discriminating, rotating, fragmenting handpiece that permits aspiration of tissue without damaging the surrounding wall during cataract removal surgery. Zelman et al.'s patent discloses a handpiece for phaco-emulsification of cataract tissue during cataract surgery. Dewey et al.'s patent discloses a handpiece for dermatological applications using a highly collimated laser beam. Molinary et al.'s patent discloses the use of a surface applicator to resurface tissue by injecting an abrasive material to the surface of tissue to alter the composition of said surface and simultaneously removing such material from said application surface. This reference further teaches a hand tool for removing surface human tissue by superficial abrasion, said tool comprising one through-hole for delivery of abrasive material to the skin surface.

The use of abrasive material to alter tissue composition provides several advantages that are inherent in the technique. The application of the abrasive material to tissue is more controlled and less invasive than, for example, laser applications because there is typically less damage or deformation of the tissue. To implement the resurfacing of a dermis layer using the abrasive material technique, a handpiece is used to apply and remove the abrasive material at the surface. The handpiece impinges an abrasive material at the surface of the tissue to alter the composition of said surface, while simultaneously removing such material from said application surface.

One such handpiece for abrasive tissue resurfacing is disclosed in the Molinary et al. patent. Abrasive material is pressurized by means of compressed air from a pressure generator. The abrasive material is channeled through a tubing to the handpiece. The handpiece regulates the flow of abrasive material and guides said abrasive material to contact the tissue surface. The handpiece also provides a return channel for the abrasive material and tissue particles to be removed from the tissue surface.

The role of using a handpiece for particle skin resurfacing is very significant for purposes of function, application, and esthetics. Functionally, the handpiece with the tubing includes a housing having a flow valve and a tissue resurfacing applicator. The flow valve comprises two channels: one channel to guide the flow of abrasive material to the tissue surface and the second channel to provide a return path for removal of the abrasive material. The flow regulator is configured to adjust the amount of abrasive material delivered to the tissue surface and vary the force with which the abrasive material impacts the tissue. The handpiece also comprises a surface applicator with an opening through which abrasive material strikes tissue. The handpiece is then applied to various areas of skin tissue, where the abrasive material removes tissue cells thereby resurfacing the skin tissue.

For applicability, the handpiece is generally applied by an operator for several hours each day. The procedure is typically applied to different surfaces of the human body including the stomach, legs, arms, forehead and the skin around the eyes. The amount of abrasive material and the requirements of the surface applicator are different for different areas of the body, requiring different applicators for different surfaces.

The prior art tissue removal handpieces that use abrasive material to resurface tissue possess certain deficiencies that detract from their functionality and ease of use. For example, handpieces may be made of different materials such as glass, metal or plastic. One drawback of metal handpieces is the repeated contact with multiple patients, resulting in the deposition of oxidized metal particulate matter on the tissue surface. Similarly, glass handpieces are hand-made, are inconsistent in shape, and can break during tissue resurfacing applications resulting in scratching the tissue surface. Plastic handpieces are more consistent in shape and application. However, each current plastic handpiece is designed for application to a specific tissue surface need, such as for example the stomach, while a different handpiece or part of such handpiece is applied to another tissue surface such as the tissue around the eyes.

Thus one problem frequently encountered in the use of such contemporary devices is their inability to use one handpiece for use with all tissue of the human body without at least interchanging the handpiece.

In view of the foregoing, it would be desirable to provide a handpiece for tissue particle resurfacing having multiple openings, each opening designed with different dimensions. It would also be desirable to selectively limit application of each opening to a designated one opening, such that when each such specific opening is used to resurface one respective portion of the skin tissue, all other openings are either blocked or shielded.

OBJECTS AND SUMMARY OF THE INVENTION

The present invention specifically addresses and alleviates the above-mentioned deficiencies associated with the prior art. More particularly, the present invention comprises a multipurpose handpiece for tissue particle resurfacing. The handpiece of the present invention comprises a housing, tubing for guiding the flow of abrasive material from a source to the tissue surface and back, a flow regulator to control flow of abrasive material, and a resurfacing applicator comprising multiple openings to guide and control the impact of the abrasive material on the tissue.

The tubing directs the flow of abrasive material from a pressurized source to the flow regulator, which in turn, is configured so as to inject abrasive material through one injection port and through a designated opening in the resurfacing applicator so as to strike a specific tissue. The abrasive material applied to the skin surface is then vacuumed through a second suction port and guided back to the pressurized source. The flow regulator and the resurfacing applicator are configured such that the resurfacing applicator opening that is in contact with the tissue is aligned with the injection port of the flow regulator so as to achieve consistent and optimal tissue resurfacing. Meanwhile, the resurfacing applicator openings not in use are blocked so that abrasive material does not leach out of these openings.

In a preferred embodiment, the resurfacing applicator is designed to rotate around said housing so as to align different openings with the injection port of the flow regulator, providing different impact conditions for different tissue surfaces. Additionally, the resurfacing applicator is preferably designed to lock in a fixed position during tissue resurfacing application. The resurfacing applicator may be designed for single or multiple use, and may be either removable or permanently fixed in the housing. In the preferred embodiment, the resurfacing applicator is designed such that openings are of different configurations and sizes to enable resurfacing of different tissue surfaces, such as for example the stomach tissue and the tissue around the eyes. Furthermore, the handpiece is preferably configured such that the flow of abrasive material can be temporarily stopped during delivery to allow rotation or replacement of the resurfacing applicator.

It is therefore an object of the present invention to provide a multipurpose handpiece for abrasively resurfacing tissue of one human subject with an abrasive material in a consistent and optimal way where said handpiece is operably connected to a tissue resurfacing system.

It is another object of the present invention is to provide a multipurpose handpiece for resurfacing different types of tissue of a human patient where the multipurpose handpiece comprises multiple-sized application openings. The application of a single resurfacing applicator to only one patient reduces the possibility of tissue contamination from one patient to another. Moreover, the use of multiple openings on one resurfacing applicator saves parts and money and also provides convenience and simplicity to tissue resurfacing applications.

It is yet another object of the present invention to provide a multipurpose handpiece for resurfacing tissue with one resurfacing applicator opening, while covering or blocking all other openings so as to prevent abrasive material from leaching out of the resurfacing applicator. In a preferred embodiment the openings not in use are blocked using a removable cover. Alternatively, a removable tape may be used to cover openings not in use. A third alternative embodiment includes a shield that fits either under or over the remaining openings such as to block all resurfacing applicator openings except the opening that is in use. Accordingly, such a shield comprises one or more openings differing in size, where only one shield opening overlaps a smaller resurfacing applicator opening such that said shield opening is selectively positioned in alignment with the designated opening.

It is yet another object of this invention to use different sizes and shapes of resurfacing applicator openings to correspond to different tissue applications. One possible application is to resurface tissue around the stomach area, while another application is for resurfacing tissue on the arms and legs. A further application is for tissue around the eyes. As those skilled in the art will recognize, there is no limit to the types of sizes and shapes of the resurfacing applicator openings that can be included in this patent disclosure as long as the resurfacing handpiece is capable of achieving satisfactory tissue resurfacing results.

In one embodiment of the present invention a multipurpose handpiece is provided wherein the handpiece rotates about the housing so as to align a specific resurfacing applicator opening with the flow regulator injection port. Alignment can be achieved by including bumps or tabs on the housing and grooves on the resurfacing applicator so that the bumps cooperate with the grooves to lock in a specific alignment for a specific opening. Alignment of different openings with the flow regulator are achieved by rotating the resurfacing applicator such that different combinations of grooves lock in the respective bumps. Another alternative approach to align the resurfacing applicator with the flow regulator is to key the flow regulator so as to have a fixed configuration with the housing, and then match the markings that are engraved on the resurfacing applicator with the corresponding markings on the housing. Different sets of markings are matched for different resurfacing applicator openings for resurfacing the different types of tissues.

Another object of the present invention is to provide a multipurpose handpiece for resurfacing tissue wherein a resurfacing applicator is disengagable from the housing to enable the resurfacing application to be easily replaced or exchanged. In a preferred embodiment the disengagement and interchangeability is accomplished by placing a spring retainer mechanism attached to said housing such that the force of the spring retainer results in pushing said resurfacing applicator out of a locked position.

A still another object of the present invention is to provide a multipurpose handpiece with the capability to stop the flow of abrasive material during the process of rotation, removal or interchangeability of the resurfacing applicator.

A still further object of the present invention is to add a coupling ring between resurfacing applicator and housing to facilitate the coupling, alignment, and rotation of the resurfacing applicator.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 1 is a perspective view showing the multi-purpose resurfacing handpiece;

FIG. 2 is an exploded perspective view of the multi-purpose resurfacing handpiece of FIG. 1;

FIG. 3 is a sectional view taken along the top of the multi-purpose resurfacing handpiece of FIG. 1;

FIG. 4 is a perspective view showing the resurfacing applicator of the multi-purpose handpiece of FIG. 1;

FIG. 5 is a cross sectional view of the resurfacing applicator of the multi-purpose handpiece of FIG. 1;

FIG. 6 is a perspective view showing the flow regulator of the multi-purpose resurfacing handpiece of FIG. 1;

FIG. 7 is a cross sectional view showing the flow regulator of the multi-purpose resurfacing handpiece of FIG. 1;

FIG. 8 is a perspective view showing the shield of the multi-purpose resurfacing handpiece of FIG. 1;

FIG. 9 is a perspective view showing the back view of the shield of the multi-purpose resurfacing handpiece of FIG. 1;

FIG. 10 is a cross sectional view showing of the shield of the multi-purpose resurfacing, handpiece of FIG. 1;

DESCRIPTION OF THE PREFERRED EMBODIMENTS

Figure 11:
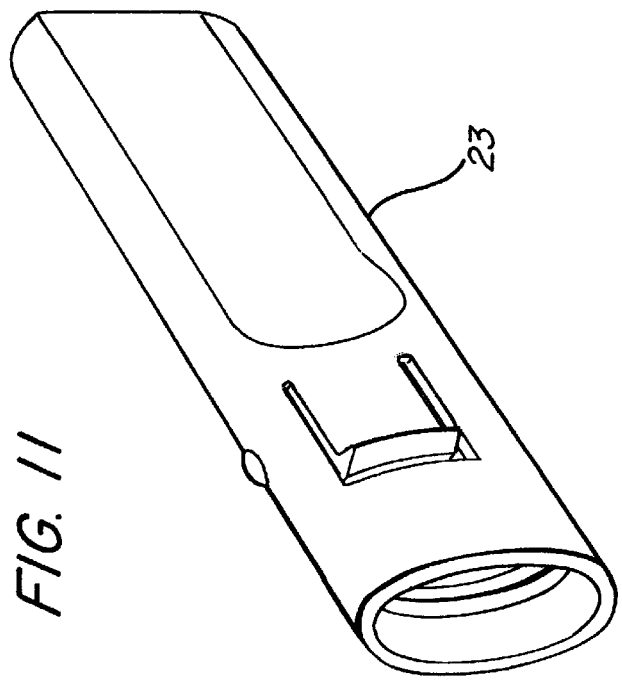
FIG. 11 is a perspective view showing the housing of the multi-purpose resurfacing handpiece of FIG. 1.
Figure 12:
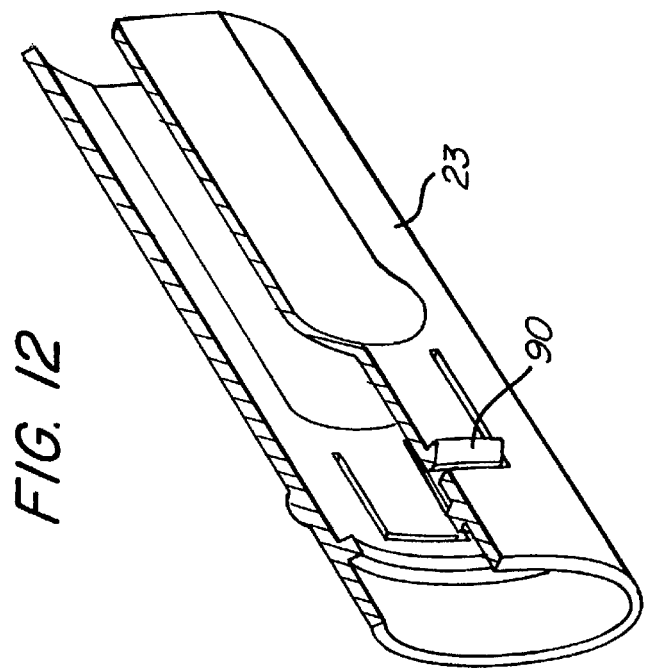
FIG. 12 is a cross sectional view showing the housing of the multi-purpose resurfacing handpiece of FIG. 1.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a multipurpose handpiece for abrasively resurfacing a tissue surface while permitting selective openings to increase the versatility of said handpiece.

Although the present invention is described and illustrated as a handpiece that utilizes abrasive material, those skilled in the art will recognize that various different abrasive and non-abrasive materials can be used to re-sculpture the tissue surface. As such, illustration and description of the present patent as a tissue resurfacing handpiece for use with abrasive material is by way of example only, and not by way of limitation. Numerous materials such as powders, aluminum oxide, grounded sea shell powder are likewise specifically contemplated herein.

Turning to the Figures, FIG. 1 shows tubing 21 which guides the flow of abrasive material from a distal vacuum/pressure generator, i.e. a pressurized source of abrasive material (not shown) to a flow regulator, and tubing 22 which provides a return path for the abrasive material. Tubings 21 and 22 are connected to a housing 23 which holds a flow regulator 31 therein. Connected to the housing 23 is a coupling ring 70 and a resurfacing applicator 40 with a plurality of openings 41,42.

FIG. 2 illustrates an exploded view of the components of a preferred embodiment of the present invention. Abrasive material enters the housing 23 through tubing 21 and is received by the flow regulator 31 at inlet barb 32. The flow regulator 31 as shown in FIGS. 6 and 7 include two channels 38, 39 for delivery of the abrasive material. Each channel includes a barb 32,33 for securely connecting the housing to the tubing and an outlet port 34,35. Outlet port 34 is used for injecting the abrasive material to the resurfacing applicator 40 and port 35 is used for vacuuming the abrasive material applied to the tissue. In a preferred embodiment, the flow regulator 31 includes a key 37 which mates with a tab 64 on a shield 60 for positioning the shield against the flow regulator 31. Similarly, a tab 46 is located on the flow regulator 31 for positioning the flow regulator 31 in the housing 23.

Shield 60 fits over ports 34,35 of the flow regulator 31 with slot 64 mating with key 37 to position the shield 60 on the flow regulator 31. The shield is shaped to form a conical shape at a delivery end to fit the resurfacing applicator 40 and provide an opening 61 in line with the flow regulator's opening. When used in connection with the resurfacing applicator 40 as described more fully below, the shield prevents the abrasive material from escaping through openings 41,42 in the resurfacing applicator 40 except that designated opening selected for the particular application. As seen in FIGS. 9 and 10, the shield is preferably formed with a shell structure.

The resurfacing applicator 40, as shown in more detail in FIGS. 4 and 5, includes a cap 47 and a coupling ring 70 to cooperate with the coupling apparatus 90 on the housing 23 to lock the resurfacing applicator 40 to the housing 23. The cap 47 comprises a ovular wall 48 terminating in a conical section 49 with a plurality of openings 41,42 which can be aligned with the channels in the shield 60 and the flow regulator 31. Notches 45 about the distal periphery of the resurfacing applicator 40 cooperate with the bumps 27 on the housing 23 to align the resurfacing applicator 40 to the housing.

FIG. 3 illustrates the mating of the respective components in an operable relationship with a cutaway portion to show the relative position and operation of the components. Abrasive material is delivered from its pressurized source through tubing 21 and into the housing 23 of the handpiece. As shown, the housing is contoured for ease in handling and positioning the handpiece with greater comfort. Inside the housing 23 the tubing 21 connects to the flow regulator 31 at inlet barb 32 (not shown). The abrasive material passes from the tubing 21 into the flow regulator and exits into opening 61 of the shield 60. The abrasive material then is forced through opening 41 where it impacts the surface of the designated tissue (not shown). Concurrently, a vacuum is applied to tubing 22 which communicates the pressure drop to the flow regulator 31 at inlet barb 33. Inlet 33 forms the beginning of channel 38 which terminates at outlet 35. Outlet 35 is aligned with opening 61 of the shield and an opening in the resurfacing applicator adjacent the opening 41. Abrasive material delivered to the surface of the tissue is collected using the vacuum to remove the material and communicate it back through the path just described to the source of the abrasive material for collection.

Flow regulator 31 and resurfacing applicator 40 are configured such that resurfacing applicator opening 41 that is in proximity with the tissue is aligned with injection port 34 of flow regulator 31 so as to achieve consistent and optimal tissue resurfacing. Meanwhile, remaining resurfacing applicator openings 42, 43 are blocked so that the abrasive material does not leach out from the resurfacing applicator 40. The resurfacing applicator 40 is designed to rotate about the coupling apparatus 90 on the housing 23 so as to align different resurfacing applicator openings with the injection port of the regulator so as to differentiate applications to different tissue surfaces.

Additionally, resurfacing applicator 40 is designed to lock in a fixed position during tissue resurfacing application by inserting the key 37 of the flow regulator 31 into one of the grooves 45 of the resurfacing applicator 40. In this manner, the resurfacing applicator 40 is designed to be temporarily or permanently replaceable so that one or more resurfacing applicators are available with one handpiece. The resurfacing applicator is designed such that openings are of different configurations and sizes so as to resurface different tissue surfaces, as for example stomach tissue which requires a larger opening, and tissue around the eyes which uses a much smaller opening. Furthermore, handpiece is configured such that flow of abrasive material can be stopped to allow rotation or replacement of resurfacing applicator. To stop the flow of abrasive material, an apparatus is provided so as to stop the flow of abrasive material prior to rotating or exchanging resurfacing applicator. One apparatus to stop the flow of abrasive material is a clamp that can be placed on the tubing. Other means for halting the delivery of the abrasive material include levers to depress the delivery tubing, and mechanical switches to open and close the tubing.

As those skilled in the art will recognize, all alternative configurations of coupling between shield and housing as well as coupling between resurfacing applicator and housing described herein are still applicable. Furthermore, the mechanical switch may be configured so as to be a part of the housing or as part of the coupling ring as alternatives to being a part of the tubing.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein. For example, there are numerous alternative configurations to (1) blocking of unused resurfacing applicator openings; (2) keying various components of the handpiece; (3) coupling between the resurfacing applicator as well as the shield, and the housing; (4) aligning the resurfacing applicator to the flow regulator infusion port; (5) locking the resurfacing applicator in place during the resurfacing application; (6) achieving interchangeability of surface applicator; and (7) stopping the flow of abrasive material during the operation of tissue resurfacing.

What is claimed is:

1. A handpiece connectable to a pressurized source of abrasive material and a vacuum for concurrently applying and removing said abrasive material to an organic surface, said handpiece comprising:

a housing;

a first tubing connected to said housing for communicating a pressurized flow of abrasive material to said handpiece, and a second tubing for evacuating said abrasive material from said handpiece;

a flow regulator disposed within said housing and operably connected to said first and said second tubing, said flow regulator regulating the flow of abrasive material delivered to said organic surface; and a resurfacing applicator operably connected to said housing adjacent said flow regulator, said resurfacing applicator including at least two delivery openings for selectively adjusting the flow of abrasive material delivered to said organic surface.

2. The handpiece of claim 1 wherein said resurfacing applicator rotates on a collar on said housing, and wherein said resurfacing applicator can be fixed on said collar such that a preferred delivery opening on said resurfacing applicator is aligned with said flow of abrasive material delivered by said flow regulator.

3. The handpiece of claim 2 wherein said handpiece includes means for blocking the flow of abrasive material from passing through all delivery openings in said resurfacing applicator except said opening aligned with said flow of abrasive material delivered by said flow regulator.

4. The handpiece of claim 1 wherein said means for blocking the flow of abrasive material comprises a shield disposed between said flow regulator and said resurfacing applicator, said shield including an aperture positioned for allowing said abrasive material to pass through one of said delivery openings while prohibiting the flow of abrasive material through the remaining delivery openings.

5. The handpiece of claim 1 further comprising a mechanical switch to selectively stop and resume the delivery of the abrasive material to the resurfacing applicator.

6. The handpiece of claim 1 wherein said resurfacing applicator is removable from said housing and replaceable.

7. The handpiece of claim 1 further comprising a coupling ring releasably connecting said housing and said resurfacing applicator.

8. A handpiece for applying an abrasive material under pressure to an organic surface and simultaneously removing said abrasive material from said organic surface, said handpiece operably connectable to a pressurized source of said abrasive material and a vacuum source, said handpiece comprising:

a housing including means for selectively stopping the flow of abrasive material through said housing, and means on said housing for releasably locking a resurfacing applicator thereon;

a flow regulator disposed within said housing for receiving said flow of abrasive material therein through, and for directing said flow of abrasive material via an injection port to a resurfacing applicator, said flow regulator further adapted to receive abrasive material collected by said resurfacing applicator and delivering said collected abrasive material to said vacuum source, said flow regulator further comprising a structure for fixedly positioning said flow regulator within said housing;

means disposed adjacent said flow regulator for selectively limiting the flow of said abrasive material through a predetermined opening in said resurfacing applicator while denying the passage of said flow through a non-selected opening in said resurfacing applicator; and said resurfacing applicator mounted on said housing adjacent said flow regulator, said resurfacing applicator comprising a plurality of openings of various sizes for selectively controlling the flow of abrasive material delivered to said organic surface, said resurfacing applicator including an opening operably connected to said vacuum source and designated for removing abrasive material applied to said organic surface.

* * * * *